United States Patent [19]

Sarath et al.

[11] Patent Number: 4,798,582
[45] Date of Patent: Jan. 17, 1989

[54] NEEDLE CARTRIDGE

[75] Inventors: Alan Sarath, Teaneck, N.J.; James A. Mawhirt, Brooklyn, N.Y.

[73] Assignee: Permark Corp. c/o Sci/Med Advances Corp., Teaneck, N.J.

[21] Appl. No.: 113,947

[22] Filed: Oct. 27, 1987

[51] Int. Cl.⁴ .......................... B43K 5/00; A61F 2/64
[52] U.S. Cl. ...................................... 604/47; 604/48; 81/9.22
[58] Field of Search .......................... 604/47, 48, 173; 128/316, 329 R, 333; 81/9.22

[56] References Cited

U.S. PATENT DOCUMENTS 4,159,659 7/1979 Nightingale ...................... 604/47 X Primary Examiner—Allen M. Ostrager
Attorney, Agent, or Firm—Schweitzer & Cornman

[57] ABSTRACT

A needle cartridge for a surgical operating pen or tatooing instrument, said cartridge having a reservoir filled with liquid pigment adapted to be discharged into the skin through a unique tri-needle assembly.

6 Claims, 2 Drawing Sheets

NEEDLE CARTRIDGE

BACKGROUND OF THE INVENTION

The present invention is directed to improvements in surgical operating instruments of the type employed heretofore in cosmetic surgery, namely, the cosmetic surgery of the type in which tatooing procedures are employed to apply eyeliner to the edges of an eyelid by implanting a pigment solution along the edge of the eyelid and/or lash line, in eyebrow replacement or enhancement; and/or in corneal tatooing. In addition, instruments of this general type have been used by dermatologists for pigmentation at graft edges, for pigmentation in connection with hair transplants; as well as for pigmentation in connection with surgical reconstruction folowing mastectomy. Still further, instruments of this type may be used by physicians in connection with outlining tumors for chemo surgery, for marking oral tumors prior to radiation therapy or chemotherapy, as well as in connection with marking insertion sites of lumbar puncture needles.

The patent literature is replete with electrical tatooing machines. Representative of the prior art are U.S. Pat. Nos. 4,204,438; 4,159,659; 4,031,783; 4,508,106; and 4,644,952.

SUMMARY OF THE PRESENT INVENTION

Surgical tatooing instrumentation, as well as general tatooing instrumentation, heretofore involved the use of needles, either singular or in an array, mounted in pens or instruments which may be hand held for dipping of the exposed needles into an appropriate pigment solution which is to be applied sub-dermally to the skin of the subject. In accordance with the principles of the present invention, the pigment solution is delivered to the needles by new and improved cartridge in which the pigment solution is contained for continuous delivery from within the instrument to the exposed needle points.

More specifically, the exposed needles of the new cartridge are advantageously and uniquely arrayed in a triangular contiguous relationship with the centers of the abutting needles forming an equilateral triangle and with the outer peripheries of the needles being held together by an enveloping delivery tube which is permanently crimped about the needles. The interstices between the needles themselves and the walls of the delivery tube form four discrete passages for the flow of pigment solution from the cartridge reservoir to the exposed surface of the needles for delivery to the skin sites being punctured by the needles.

As a further specific aspect of the invention, the delivery tube which houses and supports the needles extends from its upper end in the pigment reservoir to the needle tips for providing communication between the reservoir and the operating points of the needles. The upper end of the delivery tube is selectively closed or valved by a steel ball which prohibits flow from the reservoir to the needles when the ball is seated in the exposed upper end of the delivery tube and which permits flow of pigment to the needles when it is unseated. As a still further aspect of the invention, the reciprocation of the new cartridge by the tatooing instrument moves the steel ball from its seated position to open a "delivery valve" and also provides a positive mixing action of the pigment solution contained in the reservoir through the reciprocating movement of the ball.

For a more complete understanding of the present invention and its attendant advantages, reference should be made to the accompanying drawings taken in conjunction with the following detailed description of the invention.

DETAILED DESCRIPTION OF THE PRESENT INVENTION

Figure 1:
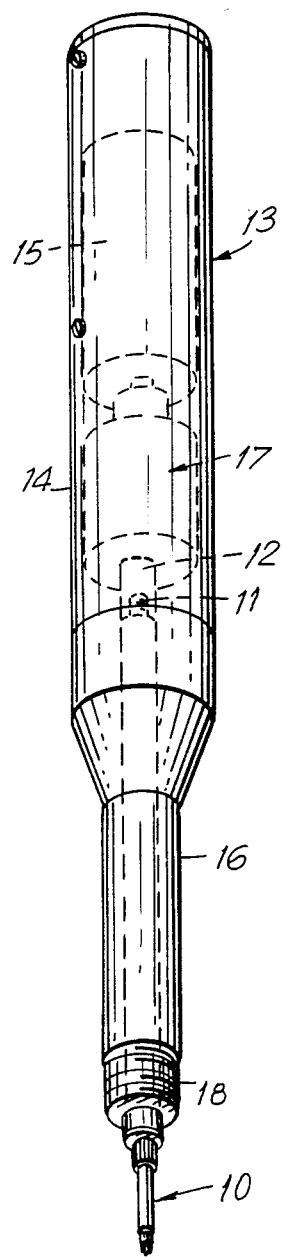
FIG. 1 is a front elevational view of a new and improved operating instrument mounting the new and improved cartridge of the present invention.

Referring initially to FIG. 1, the needle cartridge 10 of the present invention is adapted to be mounted by a threaded screw connection 11 to the drive shaft 12 of an electrical tatooing instrument 13 of the general construction shown in U.S. Pat. No. 4,644,952, the disclosure of which is incorporated by reference herein. Such an instrument 13 includes an elongated housing 14 in which an electric motor 15 is disposed for powering a reciprocating shaft assembly 16 through an associated rotating cam assembly 17, the mechanical details for which may be discerned from the aforementioned U.S. Pat. No. 4,644,952. The new and improved needle assembly 10 of the present invention may be used with any reciprocating tatooing instrument or tatooing pen which is suitably modified or otherwise constructed to accept, by an appropriate threaded connection such as disclosed in FIG. 1, or otherwise by a suitable mechanical equivalent, the new and improved cartridge 10. The surgical operating instrument/tatooing pen illustrated in FIG. 1 also may be provided with a suitable nose cone (not shown) such as illustrated in the above-identified U.S. Pat. No. 4,644,952, which nose cone may be mounted over the exposed needle assembly 10 to leave only the tips of the needles projecting therethrough. The thread 18 shown in FIG. 1 will accommodate the threaded mounting of such a nose cone on the free end of the instrument.

Figure 2:
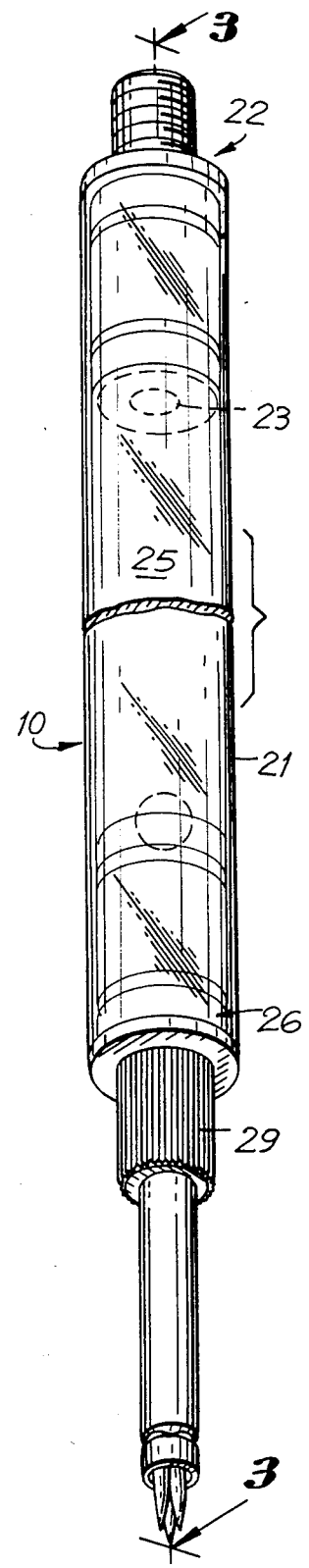
FIG. 2 is an enlarged perspective view of the new needle cartridge of the present invention.

Referring now to FIG. 2, the needle cartridge 10 of the present invention generally comprises an elongated, transparent, cylindrical reservoir tube 11 advantageously fabricated from transparent thermoplastic material to permit the viewing of the color and supply of pigmented tatooing solution housed therein. The upper end of the needle cartridge assembly is closed off by an end cap 22 which includes an orifice 23 extending completely therethrough. The orifice 23 is filled with a suitable porous filter medium 24 (see FIG. 3) to provide an air vent to the internal pigment reservoir 25 formed in the tube 21 between the upper cap 22 and a bottom cap 26. The bottom cap 26 includes a lug portion 27 which is fitted snugly within the lower end of the tube 21 and also includes an orifice 28 extending completely therethrough. Projecting downwardly from the bottom end of the tube 21 and forming a part of the end cap 26 is a straight knurled gripping portion 29 which may be used by a surgeon to hold the instrument at its lower end when a nose cap, such as described hereinabove, is not employed.

In accordance with the principles of the present invention, a steel delivery tube 30 extends through the end cap 26 to a point slightly below the innermost surface 32 of the end cap 26. The tube 30 houses and supports therein three elongated surgical steel needles 33, 34, 35 which are held together in contiguous relationship with their centers forming an equilateral triangle by crimpled wall portions 36 which are deformed inwardly and intimately about the array of needles by an appropriate cold working/crimping process.

Figure 4:
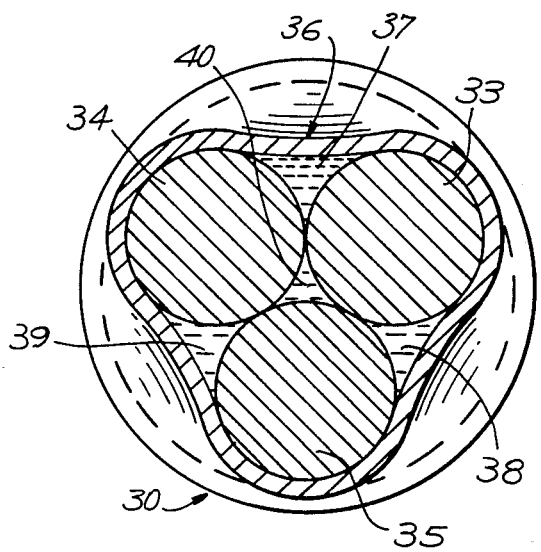
FIG. 4 is an enlarged cross-sectional view taken along line 413 4 of FIG. 3, showing the fluid delivery passage configured in accordance with the principles of the preent invention.

FIG. 4 illustrates the aforementioned interrelationship of the needles 33, 34, 35 banded by the crimped wall portion 36 in a manner whereby fluid delivery passages 37, 38, 39 and 40 are formed through the cooperation of the walls of the delivery tube 30 and the outer surfaces of the needles 33, 34, 35.

Figure 3:
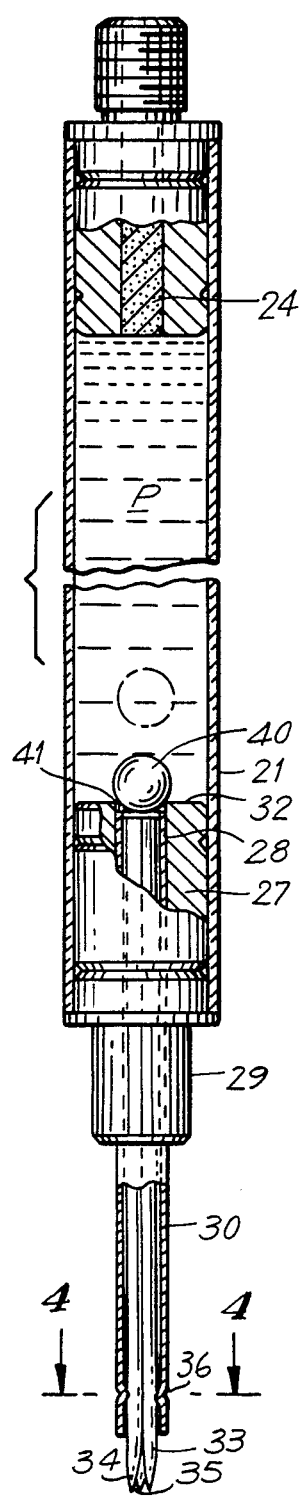
FIG. 3 is a cross-sectional view of the needle taken along line 3—3 of FIG. 2.

In accordance with the principles of the invention, a steel ball 40 is disposed within the reservoir 25 for seating in the opening 41 formed at the upper edge of the orifice 28 and at the surface 32, as best shown in FIG. 3. The ball 40, when seated in the orifice 41, closes off the reservoir 25 from the delivery tube 30 and establishes a delivery valve. However, when the motor 15 is energized to reciprocate the shaft 12 and thereby reciprocate the cartridge 10, the ball 40 is displaced and reciprocated along with the cartridge assembly, thereby opening the delivery tube 30 to communication with the pigment in the reservoir 25, as well as moving the steel ball 40 within the reservoir to provide a positive mixing of the pigment solution P ordinarily contained within the cartridge.

Advantageously, the delivery tubing 30 may be formed of hypodermic steel tubing having a diameter of 0.250 inches (outer) and 2.20 inches (inner); the needles may be No. 12 Sharps having a 0.014 inch diameter, the points of which needles as shown in the drawings are in a common plane.

It should be understood, of course, that the specific form of the invention herein illustrated and described is intended to be representative only, as certain changes may be made therein without departing from the clear teaching of the disclosure. Accordingly, reference should be made to the following appended claims in determining the full scope of the invention.

What is claimed is:

1. A needle cartridge assembly for a surgical operating pen or tatooing instrument, comprising
    (a) elongated cylindrical tube means;
    (b) an upper end cap means generally closing the top end of said tube means;
    (c) adapter means associated with said upper end cap means for mounting said needle cartridge within an operating instrument; said adapter means including an orific for air flow;
    (d) a lower plug means closing the bottom end of said tube means and forming a pigment reservoir;
    (e) liquid pigment filling said reservoir;
    (f) a thin cylindrical discharge tube passing through said lower plug means;
    (g) a tri-needle assembly comprising elongated tatooing needles supported in and projecting outwardly from said discharge tube;
    (h) a steel ball adapted to be seated in a first mode upon the upper end of said discharge tube to prevent flow of pigment from said reservoir to said needle assemble and adapted to be displaced and moved within said reservoir in a second operating mode;
    (i) a portion of said delivery tube proximate to its bottom end being crimped about and into contact with the outer surfaces of said needles thereby retaining said needles in intimate contiguous contact and cooperating therewith to define four discrete passages for pigment flow.

2. The cartridge of claim 1, in which said cylindrical tube means is fabricated of transparent plastic material.

3. The cartridge of claim 1, further characterized in that
    (a) said lower plug means has an elongated cylindrical gripping surface projecting downwardly from said tube means;
    (b) said projecting gripping surface is provided with a straight knurl.

4. The cartridge of claim 1, in which said adapter means is a threaded connector adapted for association with a reciprocating drive mechanism.

5. The cartridge of claim 1, in which said needles are approximately 0.014 inch in diameter and have sharpened tips disposed on a common plane.

6. The cartridge of claim 1, in which
    (a) an air vent is formed in said upper end cap means.
    (b) a filter means is disposed in said air vent.

* * * * *